United States Patent [19]
Misch et al.

[11] Patent Number: 5,927,979
[45] Date of Patent: Jul. 27, 1999

[54] ABUTMENT-MOUNT SYSTEM FOR DENTAL IMPLANTS

[75] Inventors: Carl E. Misch, Detroit, Mich.; J. Todd Strong, Birmingham, Ala.

[73] Assignee: Biohorizons Implants Systems, Inc., Birmingham, Ala.

[21] Appl. No.: 08/829,764

[22] Filed: Mar. 31, 1997

Related U.S. Application Data

[63] Continuation-in-part of application No. 08/356,597, Dec. 15, 1994, Pat. No. 5,628,630.

[60] Provisional application No. 60/022,219, Jul. 18, 1996, and provisional application No. 60/037,194, Mar. 5, 1997.

[51] Int. Cl.$^6$ ....................................................... A61C 8/00
[52] U.S. Cl. ............................................. 433/173; 433/172
[58] Field of Search .................................... 433/172, 173, 433/174

[56] References Cited

U.S. PATENT DOCUMENTS

| | | |
|---|---|---|
| 711,324 | 10/1902 | Lacy . |
| 866,304 | 9/1907 | Roach . |
| 2,112,007 | 3/1938 | Adams . |
| 2,347,567 | 4/1944 | Kresse . |
| 2,609,604 | 9/1952 | Sprague . |
| 2,774,141 | 12/1956 | Quinn . |
| 3,435,526 | 4/1969 | Brancato . |
| 3,499,222 | 3/1970 | Linkow et al. . |
| 3,729,825 | 5/1973 | Linkow et al. ............................. 32/10 |
| 3,732,621 | 5/1973 | Bostrom ..................................... 32/10 |
| 3,789,975 | 2/1974 | Zuest .......................................... 32/5 |
| 3,849,887 | 11/1974 | Brainin ....................................... 32/10 |
| 3,849,888 | 11/1974 | Linkow ...................................... 32/10 |
| 3,919,774 | 11/1975 | Fishman ..................................... 32/15 |
| 4,016,651 | 4/1977 | Kawahara et al. ......................... 32/10 |
| 4,053,982 | 10/1977 | Weissman .................................. 32/15 |
| 4,109,383 | 8/1978 | Reed et al. ................................. 32/10 |
| 4,177,562 | 12/1979 | Miller et al. ............................. 433/174 |
| 4,180,910 | 1/1980 | Straumann et al. ..................... 433/173 |
| 4,187,609 | 2/1980 | Edelman ................................. 433/176 |
| 4,195,367 | 4/1980 | Kraus ........................................ 3/1.91 |
| 4,204,321 | 5/1980 | Scott ....................................... 433/177 |

(List continued on next page.)

FOREIGN PATENT DOCUMENTS

| | | |
|---|---|---|
| 1 565 178 | 2/1978 | Australia . |
| 2042992 | 11/1992 | Canada . |
| 0 073 177 | 8/1982 | European Pat. Off. . |
| 28 34 890 | 3/1979 | Germany . |
| 34 23 752 | 10/1985 | Germany . |
| 30 27 138 | 3/1987 | Germany . |
| 48-438 | of 1973 | Japan . |
| 604 674 | 7/1975 | Sweden . |
| 660342 | 11/1949 | United Kingdom . |
| 757487 | 1/1953 | United Kingdom . |
| 968672 | 1/1961 | United Kingdom . |
| 937944 | 7/1962 | United Kingdom . |
| 1 203 093 | 9/1967 | United Kingdom . |
| 1 291 470 | 11/1969 | United Kingdom . |
| 1 352 188 | 4/1971 | United Kingdom . |
| 1 544 784 | 4/1977 | United Kingdom . |
| 2 063 680 | 11/1980 | United Kingdom . |
| 2 112 683 | 9/1982 | United Kingdom . |
| 2 117 641 | 2/1983 | United Kingdom . |
| 2 199 502 | 12/1987 | United Kingdom . |
| WO 85/04321 | 10/1985 | WIPO . |
| WO 86/01705 | 3/1986 | WIPO . |

*Primary Examiner*—Nicholas D. Lucchesi
*Attorney, Agent, or Firm*—Needle & Rosenberg, PC

[57] ABSTRACT

An abutment-mount for a dental implant has a longitudinally extending axis with a first end, an opposite second end and a peripheral surface. The abutment-mount is used for delivering the dental implant to a prepared site of a jawbone with an implant drive tool and is also used as a device for securing a dental prosthesis to the dental implant. The abutment-mount includes a screw, or other fastener for securing the abutment-mount to the implant. A surface is provided for attaching the dental prosthesis to the abutment-mount adjacent the first end. A structure is provided for transferring rotational force from the implant drive tool to the implant through the abutment-mount. An implant kit includes an abutment-mount, an implant and an abutment screw.

15 Claims, 4 Drawing Sheets

U.S. PATENT DOCUMENTS

| | | | |
|---|---|---|---|
| 4,259,072 | 3/1981 | Hirbayashi et al. | 433/173 |
| 4,290,755 | 9/1981 | Scott | 433/173 |
| 4,302,188 | 11/1981 | Driskell | 433/173 |
| 4,324,550 | 4/1982 | Reuther et al. | 433/174 |
| 4,334,865 | 6/1982 | Borle | 433/221 |
| 4,359,318 | 11/1982 | Gittleman | 433/173 |
| 4,416,629 | 11/1983 | Mozsary et al. | 433/174 |
| 4,431,416 | 2/1984 | Niznick | 433/173 |
| 4,468,200 | 8/1984 | Munch | 433/174 |
| 4,488,875 | 12/1984 | Niznick | 433/173 |
| 4,552,532 | 11/1985 | Mozsary | 433/173 |
| 4,573,922 | 3/1986 | Bello | 433/176 |
| 4,636,216 | 1/1987 | Tatum | 623/16 |
| 4,645,453 | 2/1987 | Niznick | 433/173 |
| 4,661,066 | 4/1987 | Linkow et al. | 433/176 |
| 4,668,191 | 5/1987 | Plischka | 433/173 |
| 4,713,003 | 12/1987 | Symington et al. | 433/174 |
| 4,713,004 | 12/1987 | Linkow et al. | 433/174 |
| 4,744,756 | 5/1988 | Ross | 433/173 |
| 4,758,161 | 7/1988 | Niznick | 433/173 |
| 4,780,080 | 10/1988 | Haris | 433/173 |
| 4,842,518 | 6/1989 | Linkow et al. | 433/173 |
| 4,856,994 | 8/1989 | Lazzara et al. | 433/173 |
| 4,863,383 | 9/1989 | Grafelmann | 433/174 |
| 4,872,839 | 10/1989 | Brajnovic | 433/173 |
| 4,904,187 | 2/1990 | Zingheim | 433/173 |
| 4,908,030 | 3/1990 | Linkow et al. | 623/16 |
| 4,915,628 | 4/1990 | Linkow et al. | 433/173 |
| 4,932,868 | 6/1990 | Linkow et al. | 433/174 |
| 4,944,754 | 7/1990 | Linkow et al. | 623/16 |
| 4,960,381 | 10/1990 | Niznick | 433/174 |
| 4,976,739 | 12/1990 | Duthie, Jr. | 623/16 |
| 4,995,810 | 2/1991 | Soderberg | 433/141 |
| 5,022,860 | 6/1991 | Lazzara et al. | 433/174 |
| 5,030,095 | 7/1991 | Niznick | 433/173 |
| 5,061,181 | 10/1991 | Niznick | 433/173 |
| 5,062,800 | 11/1991 | Niznick | 433/141 |
| 5,071,350 | 12/1991 | Niznick | 433/173 |
| 5,076,788 | 12/1991 | Niznick | 433/173 |
| 5,078,607 | 1/1992 | Niznick | 433/174 |
| 5,104,318 | 4/1992 | Piche et al. | 433/174 |
| 5,106,300 | 4/1992 | Voitik | 433/173 |
| 5,108,288 | 4/1992 | Perry | 433/173 |
| 5,116,225 | 5/1992 | Riera | 433/173 |
| 5,178,539 | 1/1993 | Peltier et al. | 433/173 |
| 5,180,303 | 1/1993 | Hornburg et al. | 433/173 |
| 5,194,000 | 3/1993 | Dury | 433/173 |
| 5,195,891 | 3/1993 | Sulc | 433/173 |
| 5,195,892 | 3/1993 | Gersberg | 433/174 |
| 5,197,881 | 3/1993 | Chalifoux | 433/173 |
| 5,199,873 | 4/1993 | Schulte et al. | 433/174 |
| 5,205,745 | 4/1993 | Kamiya et al. | 433/173 |
| 5,205,746 | 4/1993 | Chanavaz | 433/174 |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,221,204 | 6/1993 | Kruger et al. | 433/173 |
| 5,232,364 | 8/1993 | Rosen | 433/173 |
| 5,238,405 | 8/1993 | Marlin | 433/173 |
| 5,242,303 | 9/1993 | De Buck | 433/173 |
| 5,246,369 | 9/1993 | Poulmaire | 433/173 |
| 5,246,370 | 9/1993 | Coatoam | 433/173 |
| 5,254,005 | 10/1993 | Zuest | 433/173 |
| 5,259,759 | 11/1993 | Jorneus et al. | 433/173 |
| 5,269,685 | 12/1993 | Jorneus et al. | 433/174 |
| 5,269,686 | 12/1993 | James | 433/174 |
| 5,282,746 | 2/1994 | Sellers et al. | 433/172 |
| 5,286,196 | 2/1994 | Brajnovic et al. | 433/173 |
| 5,292,252 | 3/1994 | Nickerson et al. | 433/173 |
| 5,302,126 | 4/1994 | Wimmer et al. | 433/173 |
| 5,302,127 | 4/1994 | Crisio, Jr. | 433/173 |
| 5,302,128 | 4/1994 | Suga | 433/176 |
| 5,312,254 | 5/1994 | Rosenlicht | 433/173 |
| 5,334,024 | 8/1994 | Niznick | 433/173 |
| 5,368,160 | 11/1994 | Leuschen et al. | 206/339 |
| 5,409,377 | 4/1995 | Mays | 433/220 |
| 5,437,550 | 8/1995 | Beaty et al. | 433/141 |
| 5,447,435 | 9/1995 | Brodbeck | 433/173 |
| 5,462,436 | 10/1995 | Beaty et al. | 433/141 |
| 5,527,182 | 6/1996 | Willoughby | 433/172 |
| 5,538,428 | 7/1996 | Staubli | 433/173 |
| 5,558,230 | 9/1996 | Fischer et al. | 226/570 |
| 5,564,921 | 10/1996 | Marlin | 433/172 |
| 5,566,500 | 10/1996 | Niznick | 433/173 |
| 5,571,016 | 11/1996 | Ingber et al. | 433/173 |
| 5,692,904 | 12/1997 | Beaty et al. | 433/141 |
| 5,725,375 | 3/1998 | Rogers | 433/172 |
| 5,733,124 | 3/1998 | Kwan | 433/173 |
| 5,810,589 | 9/1998 | Michnick et al. | 433/169 |
| 5,816,809 | 10/1998 | Sapkos | 433/172 |

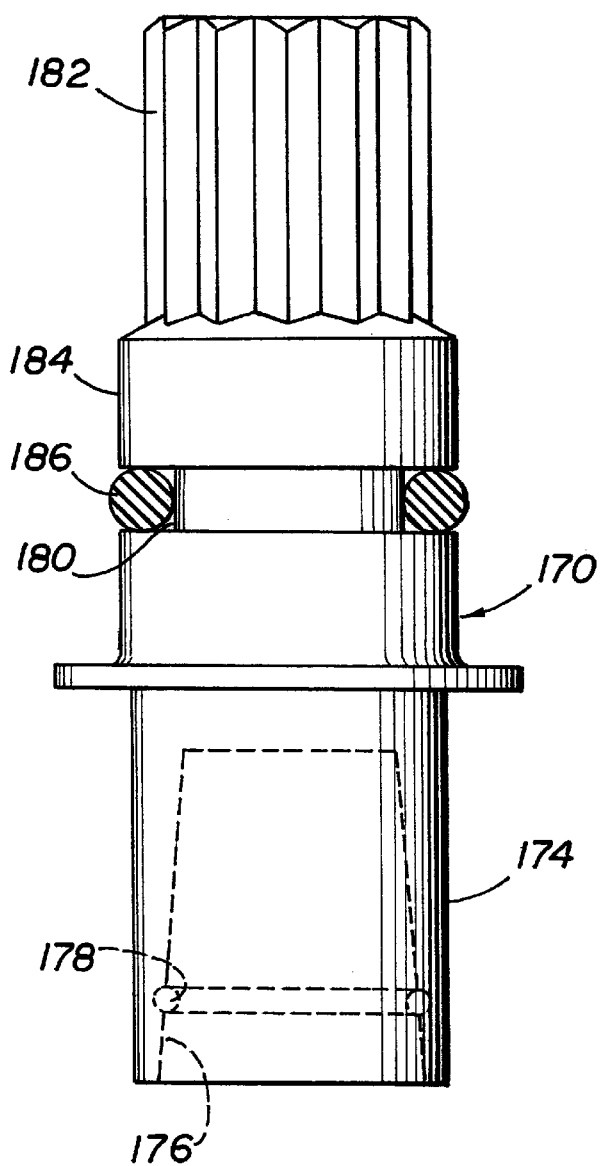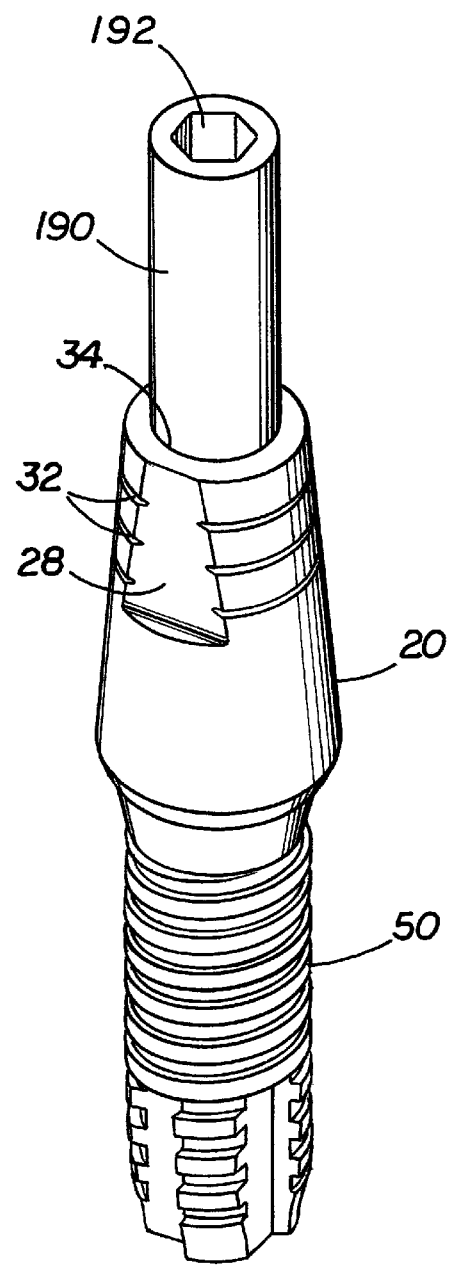
FIG 5    FIG 6

ABUTMENT-MOUNT SYSTEM FOR DENTAL IMPLANTS

CROSS-REFERENCE TO RELATED APPLICATION

This is a continuation-in-part of our application Ser. No. 08/356,597 filed Dec. 15, 1994, now U.S. Pat. No. 5,628,830 the disclosure for which is incorporated herein by reference.

CROSS-REFERENCE TO PROVISIONAL APPLICATIONS

This application for letters patent claims priority under 35 U.S.C. §119(e) on a provisional patent application, Ser. No. 60/022,219, filed on Jul. 18, 1996. This application also claims priority under 35 U.S.C. §119(e) on a provisional patent application filed Mar. 5, 1997 entitled "Dental Implant System" Ser. No. 60/037,194.

BACKGROUND OF THE INVENTION

1. Field of the Invention

The present invention relates to skeletal implants (such as dental implants) and more particularly to a dental implant kit that provides an abutment that also acts as a mount.

2. Description of the Prior Art

Dental implants are used to provide a platform to which a dental prosthesis may be secured to underlying bone in the mandible or maxilla of a dental patient. A typical root form dental implant system employs a dental implant that is placed in a prepared site in the underlying bone. A disposable mount is used to provide a connection to an insertion tool used to place the implant into the bone. If the implant is a threaded implant, the mount is typically a removable extension of the implant that provides a hex nut-type suface for engagement with a socket used for screwing the implant into the prepared site. Once the implant is engaged in the site, the mount is removed and discarded. A cover screw is affixed to the top of the implant and the bone surrounding the prepared site is allowed to grow into the implant for several months, thereby securing the implant to the bone.

Once the surrounding bone has sufficiently engaged the implant, the cover screw is removed and an impression coping is affixed to the implant. An impression of the implant and the surrounding teeth is taken and a dental prosthesis is constructed using the impression as a model of the area of the patient's mouth surrounding the implant site. The dental prosthesis is then affixed to the abutment with cement, or other affixing means. Thus, the abutment acts as a platform for securing a dental prosthesis to the implant.

The current method is wasteful and costly because the mount is discarded and a separate abutment must be procured.

SUMMARY OF THE INVENTION

The present invention is an abutment-mount for a dental implant, having a longitudinally extending axis with a first end, an opposite second end and a peripheral surface. The abutment-mount is used for delivering the dental implant to a prepared site of a jawbone with an implant drive tool and is also used as a device for securing a dental prosthesis to the dental implant. The abutment-mount includes a screw, or other fastener, for securing the abutment-mount to the implant. A surface is provided for attaching the dental prosthesis to the abutment-mount adjacent the first end. A structure is provided for transferring rotational force from the implant drive tool to the implant through the abutment-mount.

In another aspect of the invention a groove, defined by the peripheral surface of the abutment-mount, is disposed circumferentially about the peripheral surface of the abutment-mount, thereby providing an attachment surface for cement used to affix the dental prosthesis to the abutment-mount adjacent the first end.

Yet another aspect of the invention is a dental implant kit for use with an implant drive tool. The kit includes a dental implant having a crestal end defining a first engagement surface. The kit also includes an abutment-mount, having a first end and an opposite second end, and a peripheral surface, the second end defining a second engagement surface matingly engageable with the first engagement surface, the peripheral surface defining a surface for engagement with the implant drive tool. The kit also includes a surface for securing the abutment-mount to the dental implant, thereby providing a platform for attachment of a dental prosthesis to the implant.

An additional aspect of the invention provides a method of deploying and using a dental implant in prepared site of a bone. The dental implant, having an abutment-mount coupled to the dental implant that transfers any rotational force received by the abutment-mount to the dental implant, is placed into the prepared site. Rotational force is applied to the abutment-mount with an implant drive tool, thereby rotating the dental implant into the prepared site. The abutment-mount is removed from the dental implant for a preselected period to allow bone growth into the dental implant, thereby affixing the dental implant to the bone. The abutment-mount is re-coupled to the implant and is then secured to the dental implant. A dental prosthesis is then affixed to the abutment-mount.

In yet another aspect of the invention, longitudinal force is applied to the abutment-mount with an implant drive tool, thereby driving the dental implant into the prepared site.

One advantage of the invention is that the mount used to drive the implant into the prepared site is also used as an abutment for securing the prosthesis to the implant, thereby reducing the cost of implantation.

Another advantage of the invention is that it provides an abutment that can be secured in an impression material as part of a direct or indirect impression technique.

These and other advantages will become apparent from the following description of the preferred embodiment taken in conjunction with the following drawings, although variations and modifications may be effected without departing from the spirit and scope of the novel concepts of the disclosure.

BRIEF DESCRIPTION OF THE FIGURES OF THE DRAWINGS

FIG. 5 is a front elevational view of a second embodiment of a socket for use with a ratchet.

FIG. 6 is a top front perspective view of an implant and an abutment-mount using an elongated screw as part of a direct impression technique.

DETAILED DESCRIPTION OF THE PREFERRED EMBODIMENTS

Figure 1:
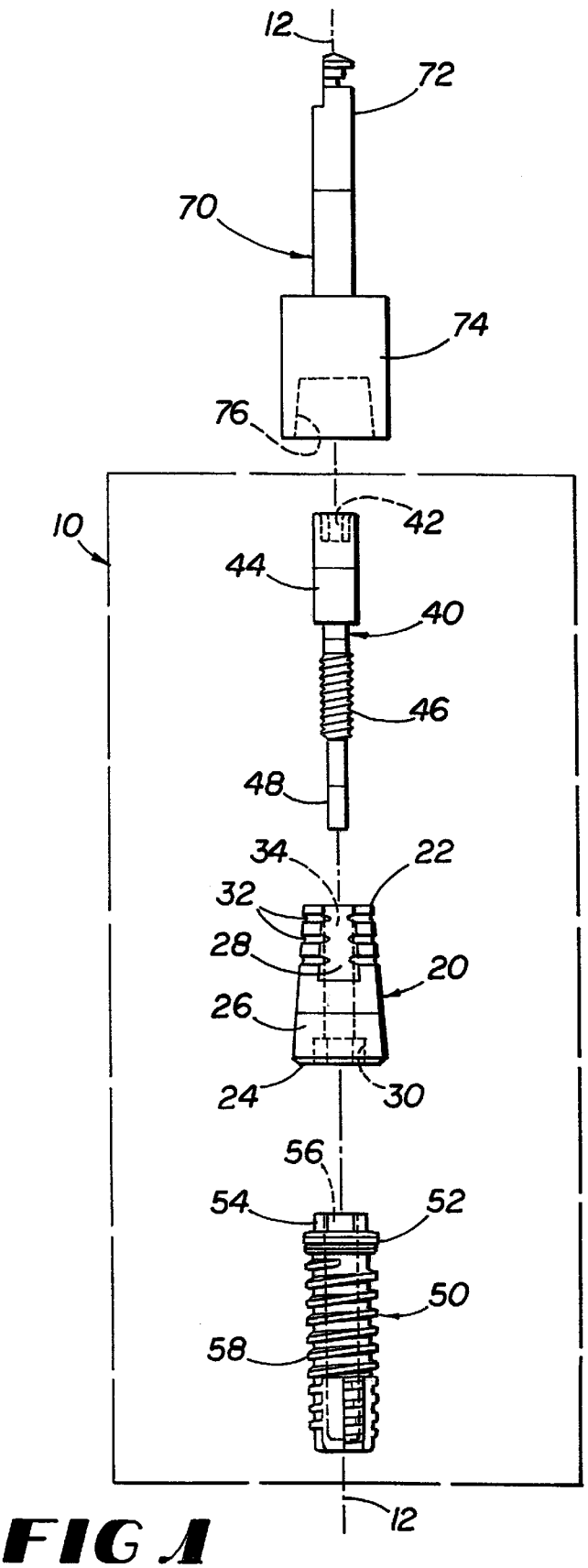
FIG. 1 is an exploded elevational view of an implant, an abutment-mount, an abutment screw and a socket for engaging the abutment-mount.

A preferred embodiment of the invention is now described in detail. Referring to the drawings, like numbers indicate like parts throughout the views. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise. Also, "complimentary in shape" means generally having compatible dimensions, without necessarily having an identical shape.

Figure 2:
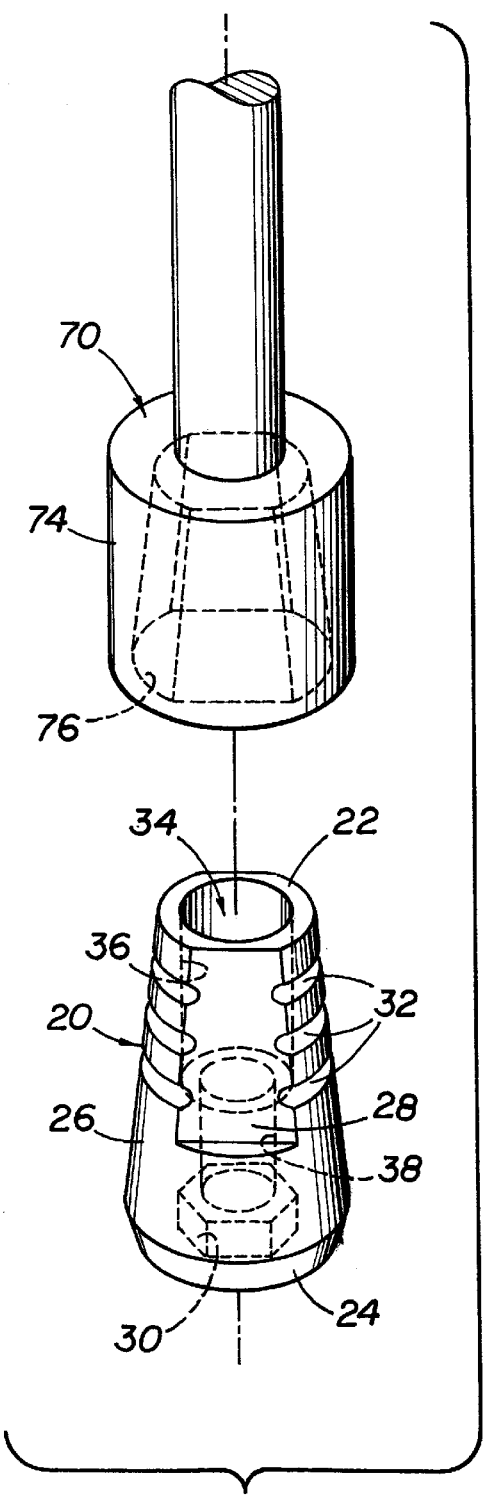
FIG. 2 is a top front perspective view of an abutment-mount and a socket.

As shown in FIGS. 1 and 2, the implant kit 10 of the present invention comprises a dental implant 50, an abutment-mount 20 and an abutment screw 40. The dental implant 50 may be one of several types, including the screw-type root-form dental implant shown. As show, the dental implant 50, the abutment-mount 20 and the abutment screw 40 are all aligned along a common axis 12. The implant 50, the abutment-mount 20 and abutment screw 40 would be made from a material suitable for implant applications, such as ASTM F-136 titanium alloy using a CNC machining process. As would be obvious to one skilled in the art, other materials and manufacturing processes may be employed without departing from the scope of the invention.

The abutment-mount 20 has a first end 22, an opposite second end 24 and a peripheral surface 26. At least one drive tool engagement surface 28 is provided for engagement with an implant drive tool 70, such as a socket. The engagement surface 28 could be a flat chordal surface, as shown, or any other of the many types of drive tool engagement surfaces that are commonly known to the arts of fastener design and implantology (for example, an internal hex could be employed for engagement with an Allen wrench as a drive tool).

The implant 50 includes a crestal end 52 and a first rotational engagement surface 54 adjacent the crestal end 52. The crestal end 52 defines a first longitudinal opening 56 with internal threads for receiving the abutment screw 40 therein. The abutment-mount 20 includes a second rotational engagement surface 30 that is complimentary in shape to the first rotational engagement surface 54. The first rotational engagement surface 54 may be a male polygonal surface (such as a hexagonal protrusion) extending from the crestal end 52, with the second rotational engagement surface 30 being a corresponding female engagement surface defined by the second end 24. Similarly, the first rotational engagement surface 54 could be a female polygonal surface, while the second rotational engagement surface 30 is a corresponding male polygonal surface. As would be obvious, many other types of engagement surfaces (including non-polygonal surfaces) could be employed with satisfactory results.

The abutment-mount 20 may be provided with one or more grooves 32 defined by the peripheral surface 26 to provide additional surface area on the abutment-mount 20 for cementing a dental prosthesis (not shown) thereto and for retention of impression material. Because the abutment-mount 20 performs both the function of an abutment, for securing a prosthesis to the implant 50, and the function of a mount, for driving the implant 50 into a prepared bone site, the present invention avoids the cost of supplying an additional, non-reusable mount.

The abutment-mount 20 is fastened to the implant 50 with the abutment screw 40. The abutment screw 40 may include a head portion 44, a threaded portion 46 and a non-threaded alignment portion 48 for aligning the threads of the threaded portion 46 with the threads in the first longitudinal opening 56 of the implant 50. The head portion 44 defines an internal hex opening 42 for receiving a hex driver for screwing the abutment screw 40 into the first longitudinal opening 56 implant 50. The abutment-mount 20 defines a second longitudinal opening 34 passing therethrough, for receiving the abutment screw 40 therein. The second longitudinal opening 34 includes an enlarged top part 36 opening to the first end 22 and a narrowed part 38 opening to the second rotational engagement surface 30. The enlarged top part 36 has a diameter sufficient to receive the head portion 44 of the abutment screw 40, while the narrowed part 38 has a diameter sufficient to receive the threaded portion 46 of the abutment screw 40. The length of the enlarged part 36 is such that the head portion 44 is substantially flush with the first end 22 of the abutment-mount 20 when the abutment screw 40 and the abutment-mount 20 are properly affixed to the implant 50.

Figure 3:
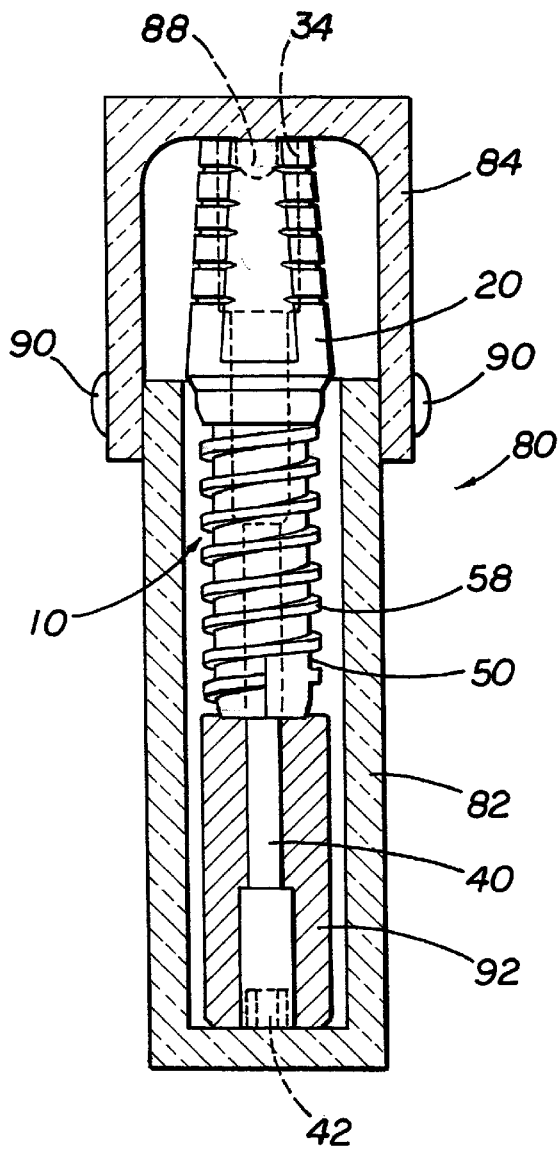
FIG. 3 is a cross-sectional view of an implant kit packaged in a vial.

As shown in FIG. 3, the implant kit 10, including the implant 50, the abutment-mount 20 and cover screw 40 may be shipped together in a package 80 comprising a vial 82 and a cap 84. The vial 82 may be made of a plastic polymer, such as polyethylene, or any other suitable material commonly known to the art. At least one tab 90 extends outwardly from the cap 84 to prevent rolling of the package 80 when placed on a flat surface.

A detente 88 extends from the center of the inside surface of the cap 84. The detente 88 is shaped to fit into the second longitudinal opening 34 of the abutment-mount 20, so that the detentes 88 holds the kit 10 and prevents the threads 58 of the implant 50 from touching the inner surface of the vial 82. This is especially important, because the threads may be coated with a coating, such as an apatite compound, that could flake is touched by the vial 82. The abutment screw 40 is held in place by a plastic holder 92 that is polygonally-shaped (e.g. having a hexagonal shape) to prevent rolling of the holder and the abutment screw 40 when they are placed on a flat surface.

Figures 4A, 4B:
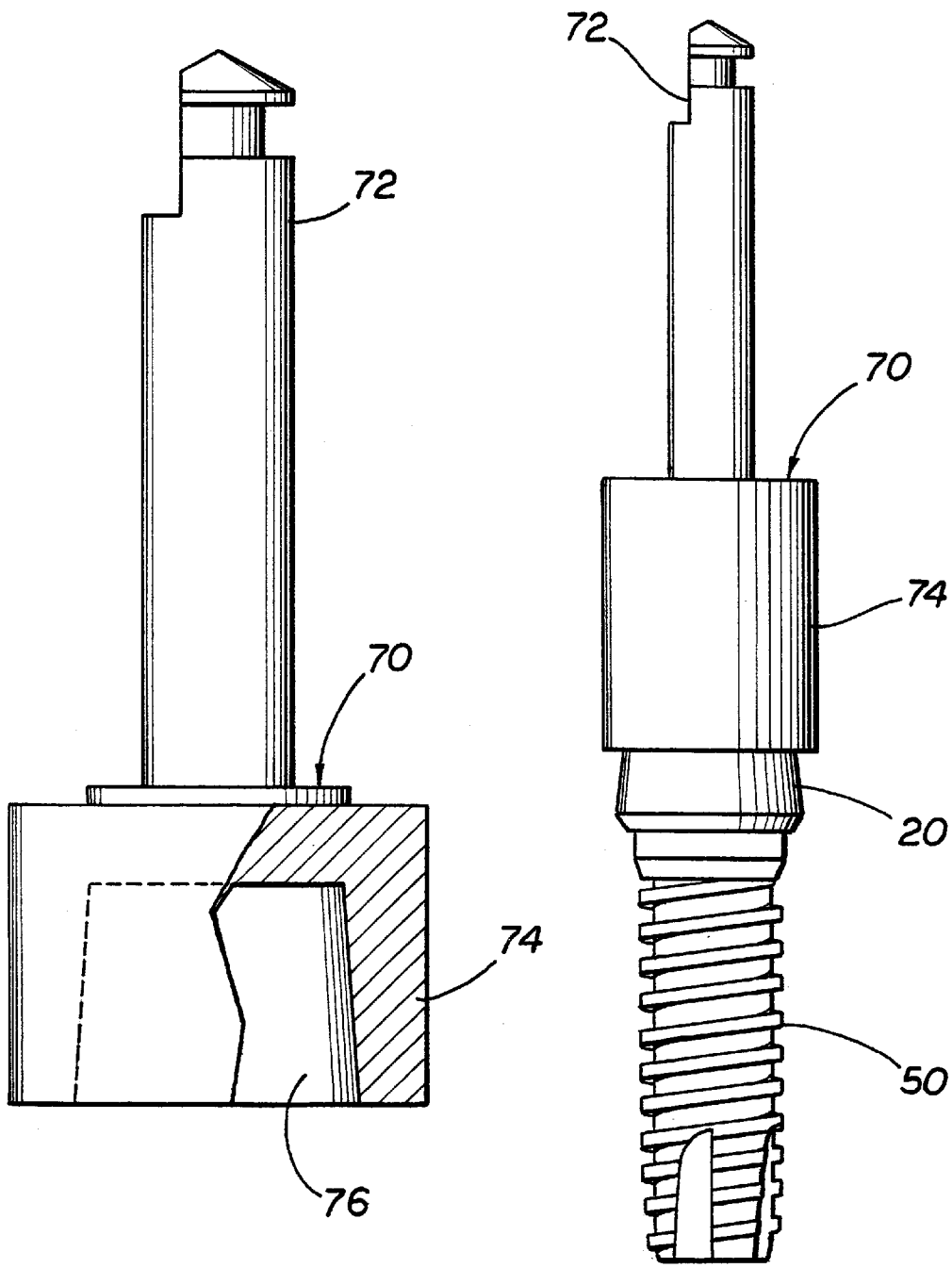
FIG. 4A is a partial cut-away elevational view of a first embodiment of a socket for use with a dental hand piece.
FIG. 4B is an elevational view of the socket of FIG. 4A engaged with an abutment-mount affixed to an implant.

As shown in FIGS. 4A & 4B, in one embodiment designed for use with a standard dental handpiece (not shown), the drive tool 70 used to drive the implant 50 includes a socket 74 defining an opening 76 that is complimentary in shape to, and fits over, the abutment-mount 20. Extending upwardly from the socket 74 is a fitting 72 that couples to the dental handpiece. The fitting 72 shown herein is designed to be coupled to an ISO 1791-1 standard dental handpiece.

In an alternate embodiment, shown in FIG. 5, a drive tool 170 for use with a ratchet (not shown) may also be used. The drive tool 170 comprises a body portion 184, for engaging the ratchet, with a socket 174 extending downwardly therefrom and a finger knurl 182 extending upwardly therefrom. A recess 180 is defined by the body portion 184 for receiving therein an O-ring 186. The finger knurl 182 may be supplied to give the implantologist the ability to start the implant by hand. The socket 174 defines a recess 176 that is complimentary in shape to the abutment-mount. The recess 176 may be provided with an o-ring 178 that acts as a spacer to allow the abutment-mount to be easily disengaged from the socket 174.

As shown in FIG. 6, an elongated screw 190 may be supplied for use as an impression pin in the direct impression technique. The elongated screw 190 fits into the second longitudinal opening 34 of the abutment-mount 20 and has a drive structure 192, such as an internal hex, for tightening and loosening the elongated screw 190. In taking an impression using the elongated screw 190, impression material (not shown) is placed around the abutment-mount 20 and the elongated screw 190 after the implant 50 has been driven into the bone. The elongated screw 190 goes through the impression material and tray so that the drive structure 192 is not covered by the impression material. Once the impression material has set, the elongated screw 190 is removed from the implant 50 and the impression material and the emplaced abutment-mount 20 is removed from the patient's mouth. The grooves 32 on the abutment-mount 20 provide a surface which improves holding by the impression material. A healing screw (not shown) is affixed to the implant 50.

While the bone is affixing the implant, a cast of the area around the implant 50 is made from the impression material. The abutment-mount 20 may fit into the cast, thereby allowing a dental prosthesis to be constructed with the abutment-mount 20 providing a base with the same relationship to the patient's mouth as it will eventually have when it is permanently affixed to the implant 50. The drive tool engagement surface 28 provides a means of ensuring that the orientation of the abutment-mount 20 remains the same with respect to the implant 50 at all times. This function could also be accomplished by machining a marking onto the abutment-mount 20 to be used as a reference point. This ensures a near exact fit between the prosthesis, the abutment-mount 20 and the patients surrounding teeth.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. An abutment-mount for a dental implant, having a longitudinally extending axis with a first end, an opposite second end and a peripheral surface, for delivery to a prepared site of a jawbone with an implant drive tool and means for securing a dental prosthesis to the dental implant, the dental implant also having a longitudinal axis, comprising:

a. means for securing the abutment-mount to the implant;
    b. means for attaching the dental prosthesis to the abutment-mount adjacent the second end; and
    c. means for transferring rotational force from the implant drive tool to the implant through the abutment-mount.

2. The abutment-mount of claim 1, wherein the abutment-mount tapers toward the first end, thereby forming a truncated cone.

3. The abutment-mount of claim 1, wherein the implant has a crestal end defining a first longitudinal opening, a portion of the opening being threaded, and the abutment-mount defines a second longitudinal opening passing therethrough between the first end and the second end and wherein the securing means comprises a screw that is passable through the second longitudinal opening and engageable with the threaded portion of the first longitudinal opening in the implant.

4. The abutment-mount of claim 1, wherein the implant has a first rotational engagement surface and the rotational force transferring means comprises:

a. at least one implant drive tool engagement surface defined on the peripheral surface of the abutment-mount for engagement with the implant drive tool; and
    b. a second rotational engagement surface on the abutment-mount adjacent the second end thereof and being matingly engageable with the first rotational engagement surface on the implant, whereby when the implant drive tool imparts rotational force on the implant drive tool engagement surface, the second rotational engagement surface of the abutment-mount imparts rotational force on the first rotational engagement surface of the implant to screw the implant into the prepared site.

5. The abutment-mount of claim 4, wherein the implant drive tool engagement surface is a chordal surface disposed on the peripheral surface of the abutment-mount.

6. The abutment-mount of claim 5, wherein the abutment-mount has a longitudinal axis and the chordal surface is parallel to the longitudinal axis of the abutment-mount.

7. The abutment-mount of claim 5, wherein the chordal surface is non-parallel to the longitudinal axis of the abutment-mount.

8. The abutment-mount of claim 4, wherein the first rotational engagement surface is a first polygonal surface and the second rotational engagement surface is a second polygonal surface complimentary in shape to the first polygonal surface.

9. The abutment-mount of claim 8, wherein the first polygonal surface is a male polygonal surface protruding from the crestal end of the implant extending along the longitudinal axis of the implant and the second polygonal surface is an opening defined by the second end of the abutment-mount, the opening having an interior female polygonal surface complimentary in shape to the male polygonal surface.

10. The abutment-mount of claim 8, wherein the first polygonal surface is a female polygonal surface extending along the longitudinal axis of the implant and the second polygonal surface is a male polygonal surface, complimentary in shape to the female polygonal surface.

11. The abutment-mount of claim 1, further comprising means for indicating to a user an alignment of the abutment-mount with the implant.

12. The abutment-mount of claim 11, wherein the indicating means comprises a marking at a preselected location on the abutment-mount so that the marking is in alignment with a geometrical feature of the dental implant when the abutment-mount is properly coupled to the implant.

13. The abutment-mount of claim 12, wherein the marking comprises a flat surface disposed on the peripheral surface of the abutment-mount.

14. An abutment-mount for a dental implant, having a longitudinally extending axis with a first end, an opposite second end and a peripheral surface, for delivery to a prepared site of a jawbone with an implant drive tool and means for securing a dental prosthesis to the dental implant, comprising:

a. means for securing the abutment-mount to the implant;
    b. a groove defined by the peripheral surface and disposed circumferentially about the peripheral surface of the abutment-mount, thereby providing an attachment surface for cement used to affix the dental prosthesis to the abutment-mount adjacent the first end; and
    c. means for transferring rotational force from the implant drive tool to the implant through the abutment-mount.

15. The abutment-mount of claim 14, further comprising means for taking an impression of the abutment-mount.

* * * * *